United States Patent [19]

Matcher et al.

[11] Patent Number: 5,706,821
[45] Date of Patent: Jan. 13, 1998

[54] SPECTROSCOPIC METHOD FOR QUANTITATIVELY DETERMINING THE CHANGE OF CONCENTRATION OF A LIGHT OR OTHER RADIATION ABSORBING COMPOUND IN A MEDIUM WHICH IS INTERROGATED THROUGH AN INTERVENING MEDIUM

[75] Inventors: Stephen John Matcher; Mark Cope; David Thomas Delpy, all of London, United Kingdom

[73] Assignee: Hamamatsu Photonics K.K., Hamamatsu, Japan

[21] Appl. No.: 366,588

[22] Filed: Dec. 30, 1994

[51] Int. Cl.$^6$ ............................................. A61B 6/00
[52] U.S. Cl. .................... 128/665; 128/664; 128/633; 356/40; 356/433; 250/330
[58] Field of Search ............................ 128/664, 665, 128/633; 356/433, 39, 40, 341, 342, 239; 250/330, 339.11, 574, 358.1

[56] References Cited

U.S. PATENT DOCUMENTS 4,805,623   2/1989   Jobsis .

OTHER PUBLICATIONS

Chance et al, "A Phase Modulation System for Dual Wavelength Difference Spectroscopy of Hemoglobin Deoxygenation in Tissues", University of Pennsylvania, Department of Biochemistry and Biophsysics, Phildelphia, PA 19104, no date.

Wary et al, "Characterization of the Near Infrared Absorption Spectra of Cytochroms aa$_3$ and Haemoglobin for the Non-Invasive Monitoring of Cerebral Oxygenation", Biochim. Biophys. Acta. 933 (1988) pp. 184–192.

Hiraoka et al, "A Monte Carlo Investigation of Optical Pathlength in Inhomogeneous Tissue and its Application to Near-Infrared Spectroscopy", Phys. Med. Biol. 38 (1993), pp. 1859–1876.

Matcher et al, "Use of the Water Absorption Spectrum to Quantify Tissue Chromophore Concentration Changes in Near-Infrared Spectroscopy", Phys. Med. Biol. 38 (1994) pp. 177–196.

*Primary Examiner*—Brian L. Casler
*Attorney, Agent, or Firm*—Cushman Darby & Cushman IP Group of Pillsbury Madison & Sutro LLP

[57] ABSTRACT

A spectrometric technique is described for quantitatively determining the change in concentration of a substance which is contained in a medium which both absorbs and scatters spectroscopically interrogated radiation, and in particular to the specific case in which the change in concentration of the substance occurs in one spatially distinct region of the medium. The medium includes a plurality of such regions displaying potentially different absorption and scattering properties to the radiation. Specific applications are disclosed involving the noninvasive determination of changes in concentration of the substances oxyhemoglobin and deoxyhemoglobin and/or changes in the redox state of the substance cytochrome oxidase within the brain or skeletal muscle, and in cases where the brain or skeletal muscle is interrogated by radiation in the near-infrared part of the electromagnetic spectrum through intervening surface tissues, i.e., cortical bone or adipose tissue, where it may be assumed that no changes of concentration of said substances occur within said surface tissues.

33 Claims, 7 Drawing Sheets

SPECTROSCOPIC METHOD FOR QUANTITATIVELY DETERMINING THE CHANGE OF CONCENTRATION OF A LIGHT OR OTHER RADIATION ABSORBING COMPOUND IN A MEDIUM WHICH IS INTERROGATED THROUGH AN INTERVENING MEDIUM

BACKGROUND OF THE INVENTION

1. Field of the Invention

This invention generally relates to a method whereby the concentration change of a substance of interest may be determined spectrometrically when the region of a medium containing the substance is subjected to light or other radiation scattering, and further wherein the medium containing the substance of interest is separated from the spectrometric measurement apparatus by an intervening light or other radiation scattering medium disposed therebetween, the intervening medium being of unknown dimensions and possessing different absorption and scattering properties to the medium of interest. A requirement of the invention is that the medium containing the substance of interest and the intervening medium should both contain a reference substance of known concentration and further that the concentration of this reference substance should differ in the medium of interest and the intervening medium.

2. Related Background Art

In many fields of science and technology there exists the need to spectrometrically determine the concentration of a substance present in a medium which scatters radiation used to illuminate the medium. In particular, there currently exists a technique known as near infrared tissue spectroscopy in which intact organs of human or animal anatomy are illuminated by light, typically in the near-infrared part of the electromagnetic spectrum, and the resulting transmitted light is spectrally analyzed to determine the concentration change of various physiologically important substances. Specific examples in the field of clinical near infrared spectroscopy include the monitoring of changes in the levels of oxygenated and deoxygenated hemoglobin in blood supplying oxygen to the brain or skeletal muscle and the monitoring of changes in the redox state of the respiratory chain enzyme cytochrome-oxidase located within the mitochondria of cells.

Such techniques are, for example, disclosed in the following references:

"U.S. Pat. No. 4,805,623"

"A phase modulation system for dual wavelength difference spectroscopy of haemoglobin deoxygenation in tissue", Chance B., Maris M., Sorge J. and Zhang M. Z. Proc. SPIE 1204 481–91, 1990";

"Characterization of the near infrared absorption spectra of cytochrome $aa_3$ and haemoglobin for the non-invasive monitoring of cerebral oxygenation, Wray S., Cope M., Delpy, D. T., Wyatt J. S. and Reynolds E. O. R. Biochim. Biophys. Acta. 933 184–92, 1988"; and "A Monte Carlo investigation of optical pathlength in inhomogeneous tissue and its application to near-infrared spectroscopy, Hiraoka M., Firbank M., Essenpreis M., Cope M., Arridge S. R., van der Zee P. and Delpy D. T. Phys. Med. Biol. 38 1859–76, 1993" etc.

SUMMARY OF THE INVENTION

The determination of the concentration of a substance in a surrounding medium by interrogating that medium with radiation to which the substance displays selective absorption is well established in the case that the surrounding medium elastically scatters the probing radiation to a negligible degree. In this case, the transmitted radiation is spectrally analyzed to yield the concentration of the radiation absorbing substance by applying the well known Beer-Lambert law:

$$A \equiv \mathrm{Log}\left(\frac{I_0}{T}\right) = C \cdot \epsilon \cdot 1 \tag{1}$$

wherein:

$I_0$=intensity of radiation incident on the sample under study.

$I$=intensity of radiation transmitted by the sample under study.

$A$=logarithmic reduction in the intensity of the radiation by the sample hereafter referred to as the "attenuation" of the radiation by the sample.

$C$=the concentration of the radiation absorbing substance of interest.

$\epsilon$=the attenuation of incident radiation brought about by the substance of interest when at unit concentration and when the radiation traverses a unit distance through this substance of unit concentration, hereafter referred to as the "specific absorption coefficient" of the substance of interest.

$l$=the physical pathlength traversed by the interrogating radiation in the medium under study from the point of entry into the medium to the point of exit from the medium.

NB hereafter refers to the product $C.\epsilon$, and will be referred to as the "radiative absorption coefficient" of the medium.

Standard analytical spectroscopy of non-scattering samples thus requires the measurement of the attenuation of the interrogating radiation and knowledge of the specific absorption coefficient of the substance of interest and the physical pathlength traversed by the interrogating radiation to yield the concentration of the substance of interest. This analysis can readily be extended to cases where the medium contains more than one substance of interest; in this case the attenuation of the interrogating radiation can be measured at several wavelengths, it being arranged that the substances of interest should exhibit differing specific absorption coefficients at these wavelengths. Using the Beer-Lambert law one can then set up a system of linear equations which can be solved using standard techniques to yield the concentrations of all substances of interest within the medium.

There is another case in which the medium containing the substance(s) of interest must be interrogated through an intervening medium which also scatters the interrogating radiation or when the medium itself consists of a plurality of distinct regions. Obvious examples of this situation in the field of clinical near infrared spectroscopy are when one desires to measure changes in concentration of oxygenated and deoxygenated hemoglobin and/or redox level changes of cytochrome oxidase in the brain or skeletal muscle. When studying the brain, the interrogating radiation must generally be applied through the intact skull. When studying skeletal muscle, the interrogating radiation must often be applied through a surface layer of adipose tissue of significant thickness. In such cases, the concepts of the "partial differential pathlength" and "partial differential pathlength factor" for each region of the medium have been described in the literature by Hiraoka et al. The physical pathlength traversed by the interrogating radiation in a specific region of the medium is lengthened by an unknown factor. This path lengthening factor is referred to as the "partial differential pathlength factor", and the resulting physical pathlength is referred to as the "partial differential pathlength". When a structure that is interrogated by radiation can be classified as consisting of more than one "region", the partial differential pathlength of radiation in that region is defined in two, formally equivalent, ways:

1. the average pathlength that the radiation traverses within that medium (i.e., the product of the average amount of time spent by the radiation within that region and the speed of propagation of the radiation within that region) and
2. the mathematical partial derivative of the overall attenuation suffered by the interrogating radiation with respect to the radiative absorption coefficient of the region.

Since the goal of quantified trend monitors is to determine changes in concentration of substance(s) of interest within specific regions of an interrogated medium (e.g. concentration changes of oxyhemoglobin and deoxyhemoglobin within the brain region of the head), then by definition 2. of the partial differential pathlength, it is apparent that one must determine the partial differential pathlength of the interrogating radiation within the region of interest in order to convert the measured changes in attenuation of the interrogating radiation into quantified changes in concentration of the substance(s) of interest.

The present invention is a method whereby spectrometric information is used, possibly in conjunction with time-of-flight or phase-delay measurements, to estimate the previously defined partial differential pathlengths in specific regions of a spectrometrically interrogated medium. The method is dependent on the presence within the specific regions of the medium of substances whose specific absorption coefficients to the interrogating radiation are known and whose concentrations within each medium are both known and distinct such that a set of linearly independent equations involving the partial differential pathlengths can be set up and unambiguously solved.

The essence of the invention rests upon an improvement to the pathlength estimation technique to F. F. Jöbsis (one specific embodiment of which is described in detail by Matcher et al), and estimates the weighted sum of the partial differential pathlengths in each separate region of the interrogated medium where the weighting factors are the concentrations of the reference chromophore in each medium. Hence if the medium contains as many reference chromophores as regions, and if the concentrations of these reference chromophores are both known and "sufficiently distinct" from each other, one can generate a set of linear simultaneous equations involving the partial differential pathlengths in each medium, the (known) concentrations of each reference chromophore and the pathlengths estimated using each reference chromophore. In this context, the phrase "sufficiently distinct" introduced above is to be taken to mean that the concentrations of the reference chromophores in each region yield a set of simultaneous equations which are mathematically non-singular.

According to the present invention, an improvement is provided over the state of the art by supplementing these pathlength estimates with the differential pathlength estimated using the previously described time-of-flight or phase-delay techniques. Since these techniques estimate the algebraic sum of the partial differential pathlengths, they can provide an extra equation involving the partial differential pathlengths which, if linearly independent of the other equations, can be included in the analysis using, for example, multi-linear regression. Alternatively, the time-of-flight or phase-delay measurement could be used in cases where the number of regions in the interrogated medium exceeds the number of available reference chromophores by one. Further applications are disclosed in which one or more of the reference compounds may be introduced into the regions of the medium from the external environment.

Figure 1:
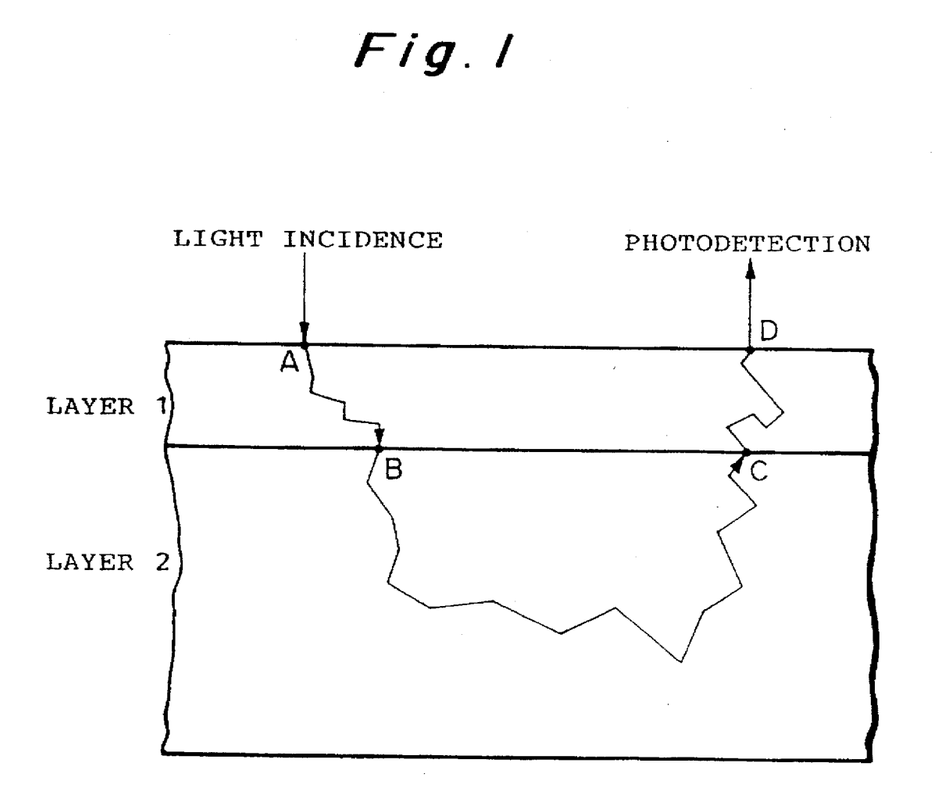
FIG. 1 shows, in schematic form, the effect of an intervening layer on the path of interrogating radiation through a medium and the relationship between partial and total differential pathlengths in the medium.
Figure 2:
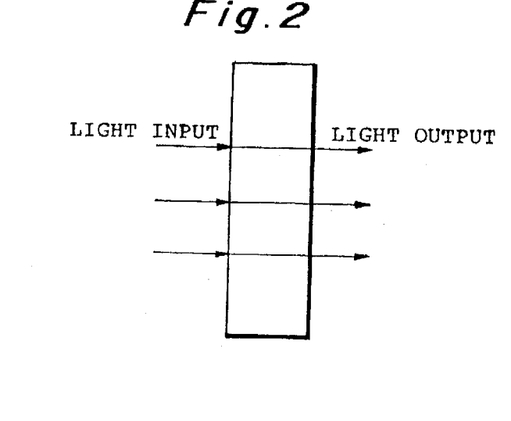
FIG. 2 shows, in schematic form, the effect of non-scattering on transillumination spectroscopy of a medium.
Figure 3:
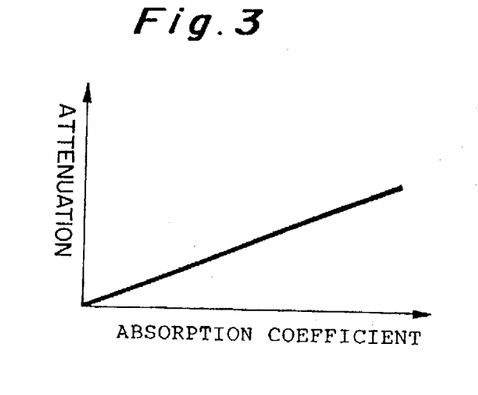
FIG. 3 shows, in graphical form, the effect of the Beer-Lamber law.
Figure 4:
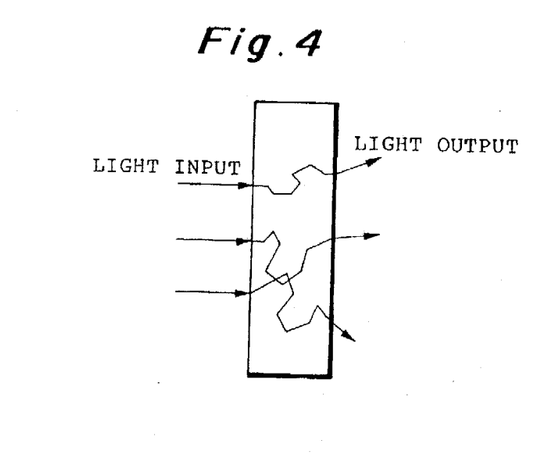
FIG. 4 shows, in schematic form, the effect of scattering on transillumination spectroscopy of a medium.
Figure 5:
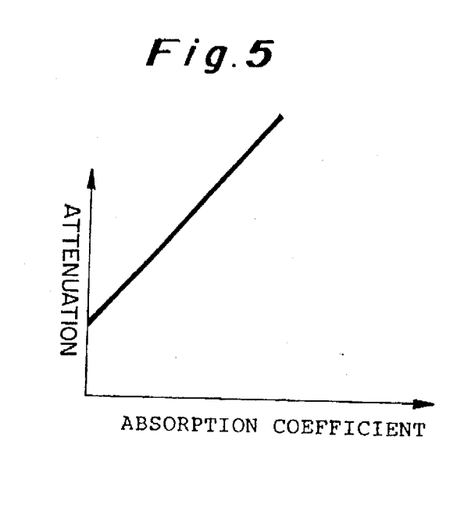
FIG. 5 shows, in graphical form, the effect of the resulting modification of the Beer-Lamber law.

FIG. 1 shows the effect of an intervening layer on the path of interrogating radiation through the medium, and the relationship between partial and total differential pathlengths in the medium. Light incident on a layer 1 which is a scattering medium is scattered at random in the layer 1 and a layer 2 which is also a scattering medium. FIG. 2 schematically shows the effect of non-scattering on transillumination spectroscopy of a medium and FIG. 3 is a graph showing the effect of the result of the Beer-Lamber law. FIG. 4 schematically shows the effect of scattering on transillumination spectroscopy of a medium, and FIG. 5 is a graph showing the effect of the resulting modification of the Beer-Lamber law. In FIG. 1, the total differential pathlength is a pathlength between a point A and a point D in FIG. 1, which is referred as $Z_{total}$ hereafter. The total differential pathlength is a sum of the partial differential pathlengths: the pathlength between the point A and a point B and the pathlength between a point C in the layer 2 and a point D which are referred as $Z_{1a}$ and $Z_{1b}$, respectively, and the pathlength between the point B and the point C, which is referred as $Z_2$. Since the pathlengths $Z_{1a}$ and $Z_{1b}$ are both within the layer 1, the sum of $Z_{1a}$ and $Z_{1b}$ shows the pathlength in the layer 1. Let the pathlength in the layer 1 be $Z_1$, and then the total partial pathlength is expressed by $$Z_{total} = Z_1 + Z_2. \tag{2}$$

Next, the method for determining the change of concentration of a scattering compound in a medium will be described. Here, the concentration of oxygenated and deoxygenated hemoglobin in the brain or skeletal muscle will be measured.

First, the total differential pathlength $Z_{total}$ is measured by a time-of-flight phase delay, or other measurement. For example, the time required for a short duration pulse of light to propagate from the point A of entry into the head to the point D of exit from the head is measured and this is multiplied by the speed of light within the head. The measurement may be performed using a mode-locked laser light source and a scanning streak camera.

Next, the intensity of absorption spectrum $A_{water}$ due to tissue water is measured. For example, the measurement may be performed using a DC lamp and a spectroscope. The intensity of absorption spectrum of water $A_{water}$ is expressed by $$A_{water} = C_{skull} \cdot \mu_{awater} \cdot Z_1 + C_{brain} \cdot \mu_{awater} \cdot Z_2 \tag{3}$$

where $C_{skull}$: concentration of water in skull (known)

$C_{brain}$: concentration of water in brain (known)

$\mu_{awater}$: absorption coefficient of water (known)

$Z_1$: pathlength traversed by the interrogating radiation in skull $Z_2$: pathlength traversed by the interrogating radiation in brain.

Thereafter, the changes $\Delta H_{HbO2}$, $\Delta H_{Hb}$ of the intensities of absorption spectra due to oxygenated and deoxygenated hemoglobin are measured. These are also measured using the DC lamp and the spectroscope.

Since $\mu_{awater}$, $C_{skull}$, and $C_{brain}$ are known values, $Z_1$ and $Z_2$ are obtained by simultaneously solving the equations (2) and (3). Since the changes in concentrations of oxygenated and deoxygenated hemoglobin mostly occur in the brain not in the skull, (i.e., substantially all of the changes in concentrations occur in the brain), the concentration changes of oxygenated and deoxygenated hemoglobin ($HbO_2$ and Hb) are precisely and quantitatively determined by dividing the measured changes of intensities due to oxygenated and deoxygenated hemoglobin by the partial differential pathlength $Z_2$.

BRIEF DESCRIPTION OF THE DRAWINGS

FIGS. 6 and 7 show, in graphical form, one specific embodiment of the differential pathlength estimation method to F. F. Jöbsis developed by Matcher et al.

DETAILED DESCRIPTION OF THE PREFERRED EMBODIMENTS

Preferred embodiments of the present invention will now be described with reference to the accompanying drawings.

Figure 6:
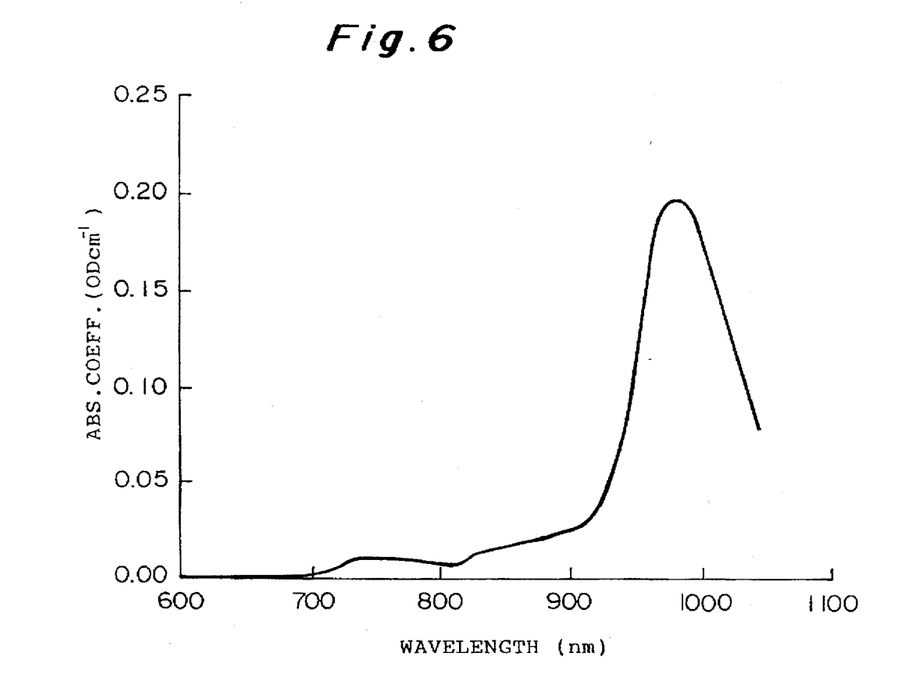
FIG. 6 shows the specific absorption coefficient spectrum of pure water and FIG. 7 shows the resulting second differential with respect to wavelength of this spectrum.
Figure 7:
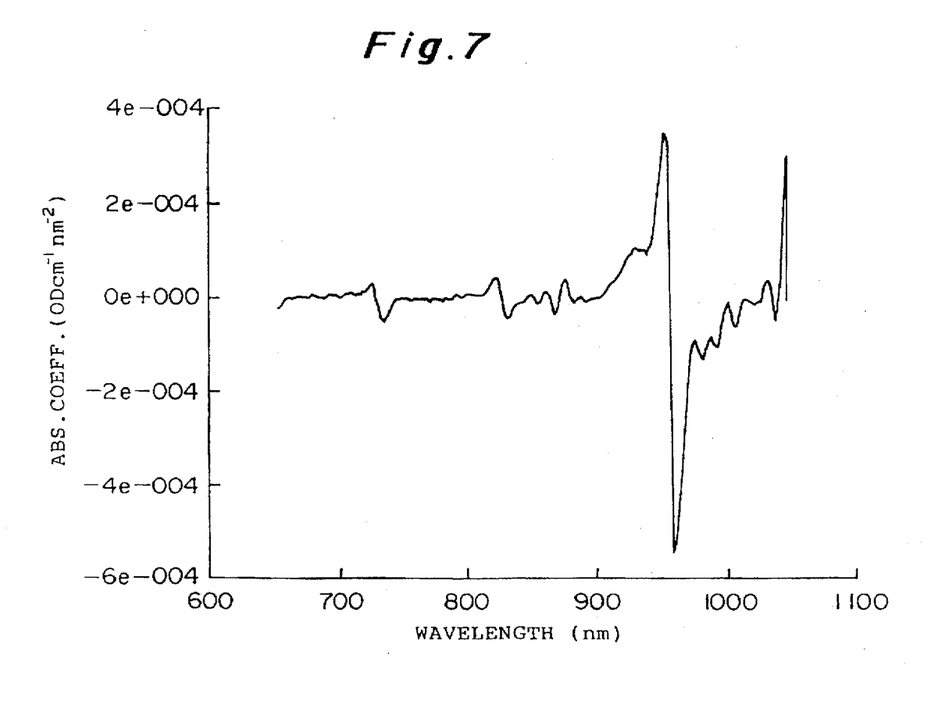

Although general in nature and scope of application, the specific application of the invention to the field of near infrared tissue spectroscopy will be described in connection with the determination of changes in oxygenation of the brain by interrogating the brain with near-infrared radiation through the intact skull. The existing technique for quantifying changes in oxygenation in the brain is to non-invasively determine the true pathlength travelled by photons in propagating from the point of entry into the head to the point of detection. This pathlength is then used in the conventional Beer-Lambert law to convert measured changes in light attenuation into changes in tissue absorption coefficient and hence to derive concentration changes of oxy- and deoxyhemoglobin. The measurement of this pathlength is currently performed in one of 3 ways:

a) by measuring the time required for a short duration pulse of light to propagate from the point of entry into the head to the point of exit from the head and multiplying this by the speed of light within the head (time-of-flight measurement). The measurement is typically performed using a mode-locked laser light source producing pulses of typical duration 10 picoseconds and a repetitively scanning streak camera with temporary resolution typically 10 picoseconds.

b) by measuring the phase delay induced in a light beam which propagates through the medium, the intensity of which is sinusoidally modulated at a typical frequency of 200MHz (phase-delay measurement). The phase delay is generally measured by cross-correlating the transmitted light signal with a reference light signal from the same light source but which has not propagated through the tissue. The pathlength traversed by the radiation within the tissue is then calculated by multiplying this phase shift (expressed as a fraction of $2\pi$) by the wavelength of the sinusoidal intensity modulation within the tissue.

c) using a specific embodiment of the method disclosed by F. F. Jöbsis in U.S. Pat. No. 4,805,623 and developed by Wray et al and Matcher et al in which the amplitude of specific spectral absorption features due to tissue water are measured and then combined with an estimate of the concentration of tissue water within the tissue to estimate the pathlength traversed by the radiation within this tissue. The specific embodiment of this method is illustrated by FIGS. 6 and 7. A near-infrared spectrometer capable of measuring light attenuation at a continuous range of wavelengths is used to obtain a near-infrared attenuation spectrum which contains specific absorption features due to tissue water (FIG. 6). Due to the previously mentioned effects of tissue scattering, this spectrum has an arbitrary baseline. To measure the amplitudes of said spectral features of water in a manner which is insensitive to the effects of this arbitrary baseline and also to improve the clarity of these features, the second differential with respect to wavelength of this tissue attenuation spectrum is formed using standard methods (FIG. 7). The specific embodiment of the method disclosed by F. F. Jöbsis developed by Matcher et al then uses the specific spectral features of water visible between 710 and 740 nm and between 810 and 840 nm. The amplitudes of these features in the measured tissue attenuation spectrum are determined by fitting them in a least-squares manner with the corresponding spectral features measured on non-scattering samples of pure water. To convert these estimates of the amplitudes of the spectral features into estimates of pathlength, the form of definition 2 of the partial differential pathlength appropriate for a medium comprising only one distinct region is employed, to wit:

$$z = \frac{\partial A}{\partial \mu_a} \quad (4)$$

since the distinct spectral features due to water in these two wavelength regions represent comparatively small changes in absorption coefficient (relative to the overall tissue absorption coefficient), equation 2 can be used to approximate the relationship between the water spectral features present in the measured attenuation spectrum ($\Delta A(\lambda)$) and their counterparts in the reference water absorption coefficient spectrum $\Delta\mu_a(\lambda)$. Since $\Delta\mu_a(\lambda)$ due to tissue water is simply the product of $\Delta\mu_{awater}(\lambda)$ (the amplitude of the absorption coefficient spectra feature for pure water) with the concentration C of water in the tissue, one has:

$$\Delta A_{water} = C_{water} \Delta \mu_{water} Z \quad (5)$$

i.e., the ratio of the amplitude of a spectral feature of water obtained from a tissue attenuation spectrum to the amplitude of this same spectral feature obtained from a pure non-scattering water sample yields the product of the differential pathlength with the concentration of tissue water in the tissue. The differential pathlength can then be estimated if the water concentration in the tissue is known.

When the medium being studied is homogeneous, i.e., possesses identical optical properties everywhere and contains a uniform distribution of absorbing chromophores, the differential pathlengths as determined by any of these three methods are equivalent and suffice to allow measured changes in transmitted light attenuation to be converted into quantified changes in tissue absorption coefficient (and hence chromophore concentration).

When the medium comprises more than one distinct region (e.g., the head consisting of a surface region comprising surface tissues and bone and a deep region comprising brain), however, the use of total pathlength determined in any of these ways will lead to erroneous underestimates of the magnitude of the changes in chromophore concentration within the brain because the total pathlength contains a contribution both from the skull and surface tissues (in which due to the relatively low perfusion of bone and skin with blood, generally no dynamic changes in oxygenation occur which are of clinical interest) and from the brain itself. Referring to the schematic diagram in FIG. 2, the total pathlength determined by methods a) and b) will measure the sum of the partial differential pathlengths $Z_{1a} + Z_{1b} + Z_2$ and hence will overestimate the partial differential pathlength in brain only, $Z_2$, which is the pathlength of interest. Hence use of this pathlength estimate with the Beer-Lambert law will lead to an underestimate of the change in absorption coefficient within the brain.

Since pathlengths $Z_{1a}$ and $Z_{1b}$ are both within skull, we will label their sum $Z_{skull}$ and hereafter refer to $Z_2$ as $Z_{brain}$. As described by Hiraoka et al, the differential pathlength obtained by the previously described time-of-flight or phase techniques (hereafter referred to as $Z_{tof}$) can be taken to present the sum of the partial differential pathlengths in the brain and skull:

$$Z_{tof} = Z_{skull} + Z_{brain} \quad (6)$$

Since these partial differential pathlengths can also be identified as the partial derivatives of light attenuation with respect to the absorption coefficients in the brain and skull and since the change of measured attenuation is related to the changes of absorption coefficient in brain and skull by:

$$\partial A = \frac{\partial A}{\partial \mu_{brain}} \cdot d\mu_{brain} + \frac{\partial A}{\partial \mu_{skull}} \cdot d\mu_{skull} \quad (7)$$

the magnitude of a water spectral feature in a measured attenuation spectrum, $\Delta A_{water}$, across the head can be written as:

$$\Delta A_{water} = C_{skull} \Delta \mu_{water} Z_{skull} + C_{brain} \Delta \mu_{water} Z_{brain} \quad (8)$$

The present invention, as specifically applied to near-infrared spectroscopic measurements on the human or animal head, involves estimating the sum of the skull and brain partial differential pathlengths in the head using a time-of-flight or phase delay technique and measuring the weighted sum of these same partial differential pathlengths using the amplitude of a specific spectral feature of tissue water at either 710–740 nm , 815–840 nm or 930–970 nm using the second differential technique described, the weighting factors being the water concentrations in the skull and the brain. Since these concentrations are quite distinct, being approximately 80% for an adult human brain and 30% for normally perfused cortical bone, the two partial differential pathlengths can be determined by solving equations (6) and (8) simultaneously.

Next, the apparatus for performing the above-described method for determining the change of concentration of the specific substance in a medium will be described. Here, the changes in concentrations of oxygenated and deoxygenated hemoglobin (Hb, $HbO_2$) in the brain are measured by interrogating the brain with near-infrared radiation through the intact skull.

Figure 8:
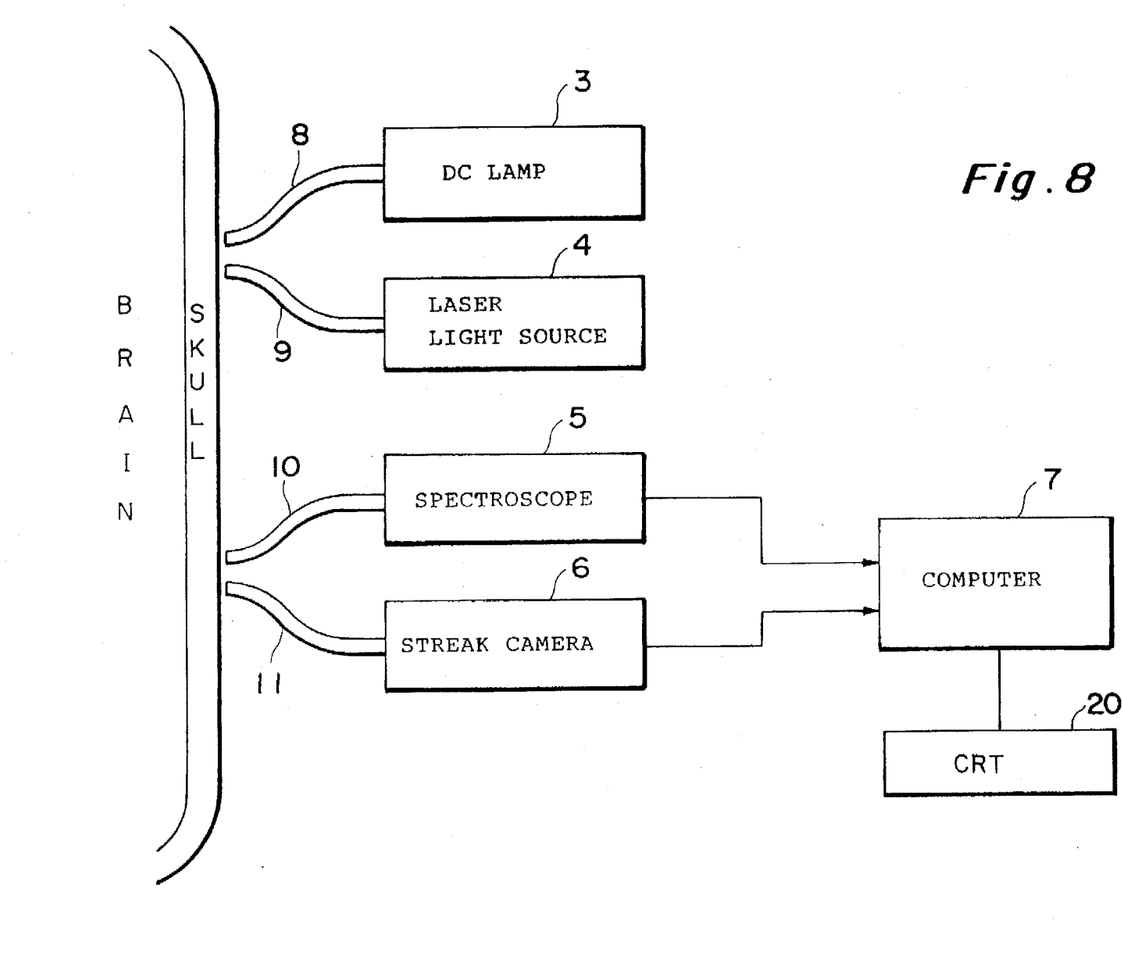
FIG. 8 shows, in schematic form, an apparatus for quantitatively determining the change of concentration of a scattering substance in a medium according to the present invention.

FIG. 8 shows a schematic diagram of an apparatus for quantitatively determining the change of concentration of a scattering substance in a medium. This apparatus comprises a DC lamp 3 for irradiating a head skin with light with a wavelength in the range of 700 nm–1050 nm , a laser light source 4 for producing pulses of duration 10 picoseconds to be applied to the head skin, a spectroscope 5 for detecting an absorption spectrum due to DC light radiation from the DC lamp 3, a streak camera 6 with temporary resolution typically 10 picoseconds for taking the time response of the pulse produced by the laser light source 4, and a computer 7 including a processor, a memory and a display, for receiving data from the spectroscope 5 and processing the data to obtain the changes in intensity of measured absorption spectrum, receiving data from the streak camera 6 to process the data to obtain the total differential pathlength traversed by the pulse radiation in the head, calculating the partial differential pathlength in a brain, and calculating the changes in concentrations of $HbO_2$ and Hb. The changes in concentration can be shown on a display unit 20, such as a CRT. In FIG. 8, reference numerals 8, 9, 10 and 11 each denote an optical fiber.

The pulses of duration 10 picoseconds from the laser light source 4 are guided to the head skin through the optical fiber 9. Then, the time responses of pulses are detected by the streak camera 6 and the data obtained are transmitted to the computer 7. The computer 7 calculates the total differential pathlength $Z_t$ traversed by the pulse radiation in the head based on the time responses of pulses. Next, the intensity of absorption spectrum of water is measured. DC light having a wavelength in the range of 700 nm–1050 nm emitted by the DC lamp 3 is incident on the head skin through the optical fiber 8. Then, the spectroscope 5 detects the light emerging from the head through the optical fiber 10 to measure the absorption spectrum due to water. The data obtained are transmitted to the computer 7. At the same time as the measurements of the absorption spectra of water, the measurement of absorption spectrum of oxygenated and deoxygenated hemoglobin $A_{HbO2}$ and $A_{Hb}$ are performed in the same manner and the results obtained are transmitted to the computer 7. With the computer 7, the measured absorption spectrum of water is spectrometrically analyzed to yield the intensity of absorption spectrum of water, and the measured absorption spectra of oxygenated and deoxygenated hemoglobin $A_{HbO2}$ and $A_{Hb}$ are spectrometrically analyzed to yield the changes in intensities of spectra of oxygenated and deoxygenated hemoglobin ($\Delta A_{HbO2}$ and $\Delta A_{Hb}$). Successively, the calculated total differential pathlength $Z_{total}$ and the changes in intensity of spectrum of oxygenated and deoxygenated hemoglobin are substituted into the equations (6) and (8) and the partial differential pathlengths $Z_{skull}$, $Z_{brain}$ are obtained. Then, the concentration changes of oxygenated and deoxygenated hemoglobin are calculated by solving the following equations (9).

$$\Delta C_{HbO_2} = \frac{\Delta A_{HbO_2}}{\mu_{aHbO2} \cdot Z_b} \quad (9)$$

$$\Delta C_{Hb} = \frac{\Delta A_{Hb}}{\mu_{aHb} \cdot Z_b}$$

In this apparatus, the optical fibers are used to guide the light, but lenses may be used instead of the optical fibers.

Figure 9:
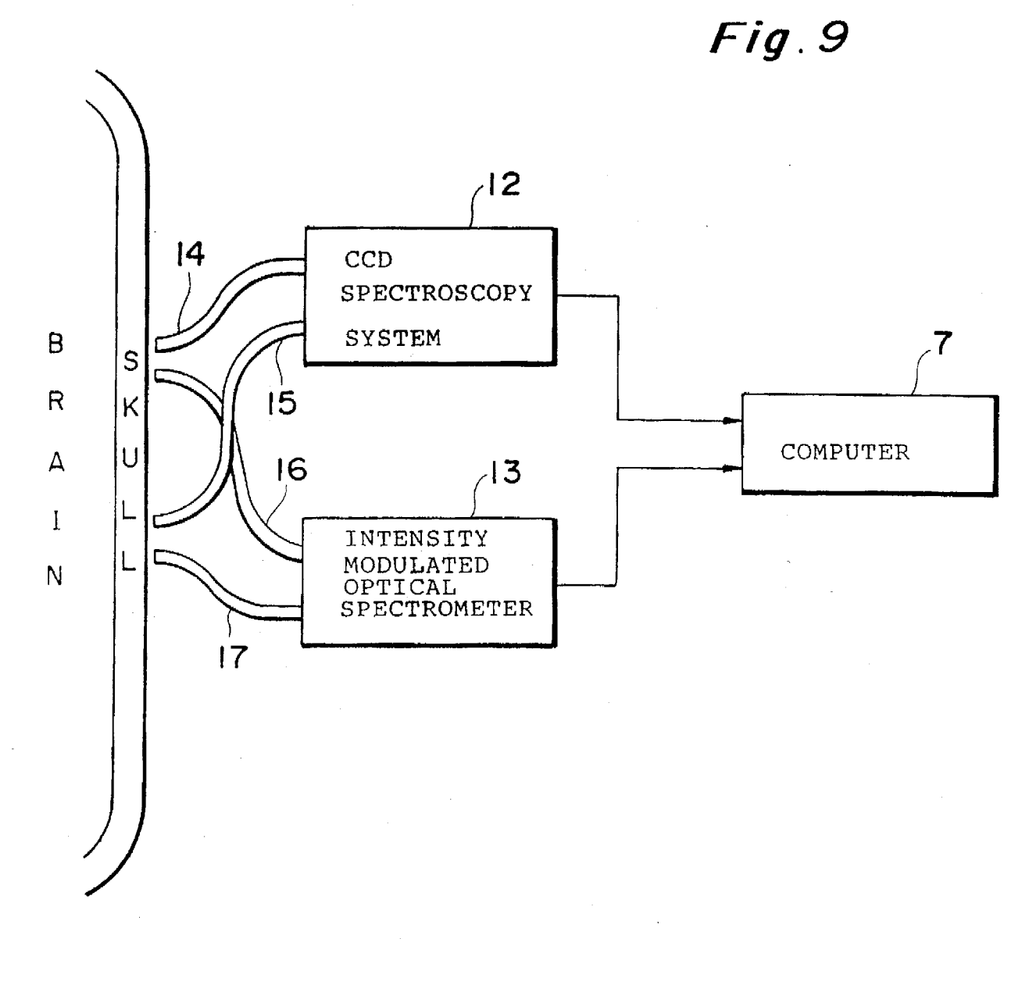
FIG. 9 shows, in schematic form, an apparatus for quantatively determining the change of concentration of a scattering substance in a medium according to the present invention.
Figure 10:
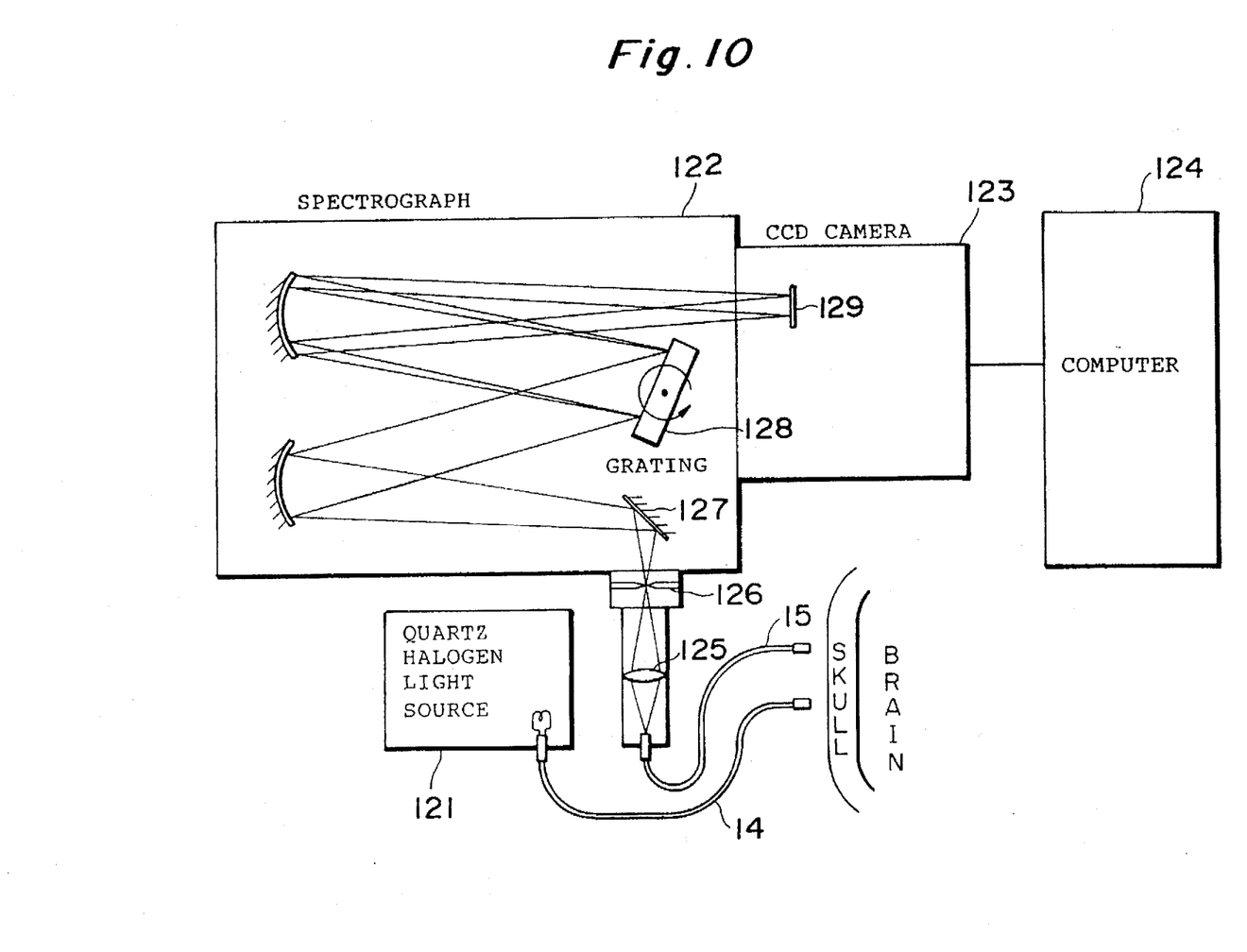
FIG. 10 shows, in schematic form, the diagram of a CCD spectroscopy system utilized in the apparatus shown in FIG. 9.
Figure 11:
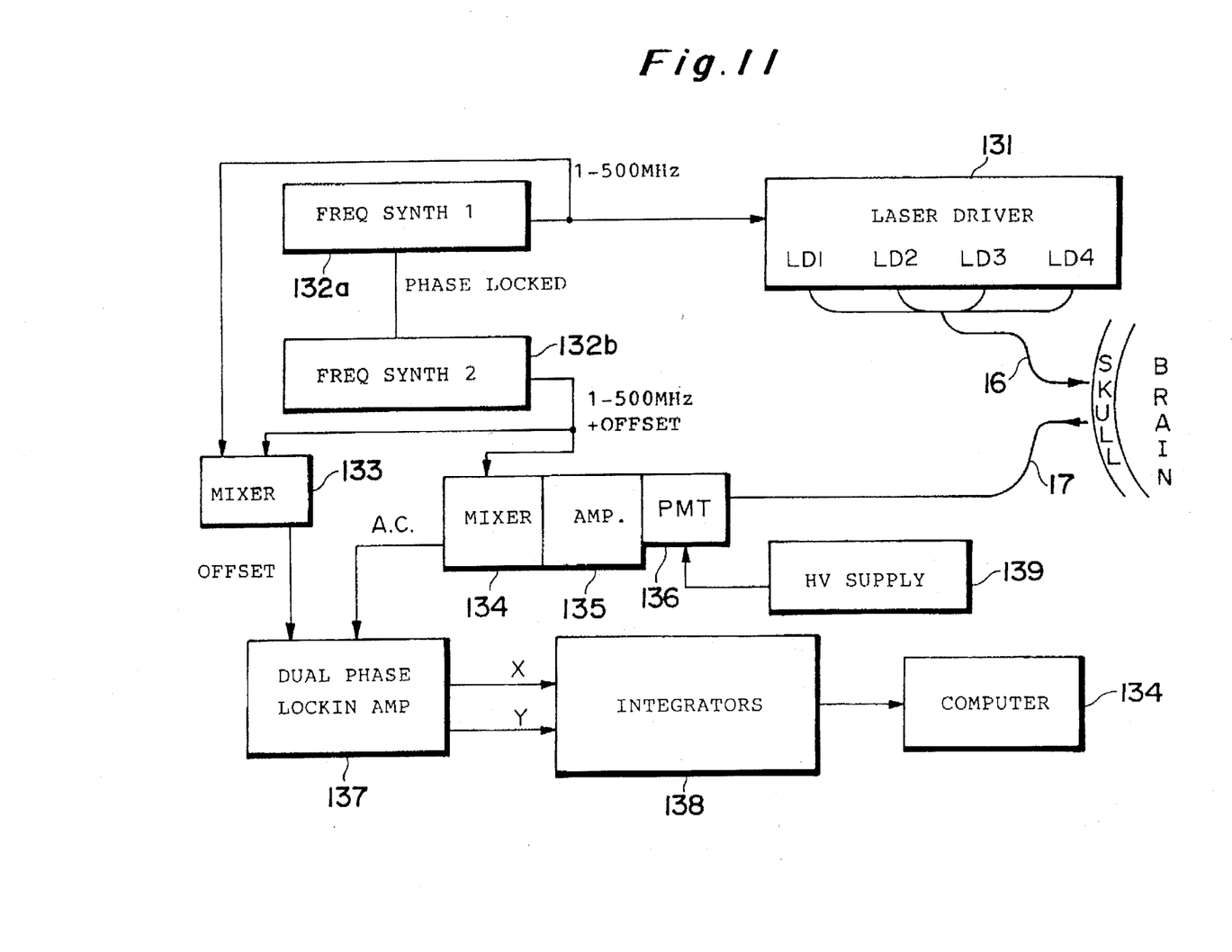
FIG. 11 shows, in schematic form, the diagram of an intensity modulated optical spectrometer utilized in the apparatus shown in FIG. 9.

The above-described method can be performed with another kind of apparatus shown in FIG. 9. This apparatus is different from the apparatus shown in FIG. 8 in that the laser light source 4 and the streak camera 6 are replaced with an intensity modulated optical spectrometer 13 and in that the DC lamp 3 and the spectroscope 5 are replaced with a CCD spectroscopy system 12. This apparatus performs the determination of the concentrations of oxygenated and deoxygenated hemoglobin in the same way as the apparatus shown in FIG. 8. The schematic diagrams of the intensity modulated optical spectrometer 13 and the CCD spectroscopy system 12 are shown in FIG. 10 and FIG. 11, respectively.

First, the intensity modulated optical spectrometer shown in FIG. 11 will be described. The intensity modulated optical spectrometer is used for the phase-delay measurement. As shown in FIG. 11, two wideband frequency synthesizers 132a and 132b provide the laser modulation frequency $\omega_0 t$ and a frequency offset $\Delta\omega_0 t$. The modulation frequency is varied between 1–500 MHz and the offset selected in the kHz region with a resolution of 100 Hz. Both synthesizers 132a and 132b are phase locked together. The signals from the frequency synthesizer 132a and the frequency synthesizer 132b are mixed via mixer 133 and filtered and passed through a comparator circuit to produce a TTL signal at the offset frequency. This is the reference signal for the dual phase lock-in amplifier 137. The frequency signals from each of the synthesizers 132a, 132b are split to intensity modulate the laser diodes LD1, LD2, LD3, LD4 and provide a frequency for mixing at the output of the photomultiplier tube (PMT) 136 with HV supply 139. There are the four laser diodes LD1, LD2, LD3, LD4 at the wavelengths 690 nm, 740 nm, 804 nm and 829 nm with variable means output powers between 6 and 40 mW. While being RF modulated, they are also time multiplexed via a counter board inside the controlling PC. Photodiodes mounted within each laser diode package allow continuous monitoring of output powers. Four separate optical fibers form a bundle 16 to carry the light with wavelength $\omega_0 t$ from las drive 131 to the head. Let the phase delay due to head be $\psi$. Then, the light emerged from the head has the frequency $\omega_0 t + \psi$. A 5 mm² fiber bundle 17 carries the detected light emerged from the head to the front face of the photomultiplier tube 136. The A.C. component carrying the detected signal at the modulation frequency $\omega_0 t + \psi$ is itself amplified at 135 and then mixed at mixer 134 with the signal having the frequency $(\omega_0 + \Delta\omega_0)t$ from the second frequency synthesizer 132b. Hence cross correlation occurs to produce the detected signal now modulated at the offset frequency, $\Delta\omega_0 t + \psi$. This signal is fed into the dual phase lock-in amplifier 137 which has been modified to have a short time constant of approximately 100 μS. The X and Y outputs of the dual phase lock-in amplifier 137 are intergrated via intergrators 138 and these signals are continuously read by the controlling computer 134 via an analogue interface card. The phase delay due to head is expressed by $\psi = \tan(Y/X)$. The phase delay $\psi$ is obtained with the computer. Then, with the computer, the total differential pathlength is obtained by solving the equation $$Z_t = C\psi/\omega_0 \quad (10)$$

where $Z_t$: total differential pathlength

C: speed of light in head $\psi$: phase delay in head $\omega_0$: frequency of light incidence on head.

Next, the CCD spectroscopy system shown in FIG. 10 will be described. This system is for measuring an absorption spectrum of a specific substance.

As shown in FIG. 10, the CCD spectroscopy system comprises a quartz halogen light source 121, a spectrograph 122, a CCD camera 123, and a computer 124. The light source is a 100 watt quarts halogen lamp with an optical fiber output. A short pass filter (not shown) with a sharp cutoff for wavelengths longer than 1000 nm removes unwanted heat from the light source. Various color glass filters (not shown) with long pass characteristics at visible wavelengths are employed to eliminated unwanted higher order spectra.

A 3 mm diameter glass fiber optic bundle 14 of high numeral aperture (NA>0.5) carries light to the head. Light emerged from the head is collected by a second fiber optic bundle 15 comprising 100 μm core silica glass fibers (NA 0.2) with a cross section changing from a circle of 1 mm diameter at the head (sample) to a 5 mm high by 100 μm slit at the input to the spectrograph 122.

The spectrograph 122 itself has a 30cm focal length with an input aperture of f/4.2. Light enters through a variable width slit 126 of micron resolution and is dispersed by a custom made ruled grating 127 of 60 lines/mm blazed at 650 nm. Detection of the dispersed light is performed by an array detector 129 at the focal point of the output mirror 128. The detector consists of a liquid nitrogen cooled silicon change coupled device (CCD) camera using a 385 by 578 array of 22 μm square elements. The 385 horizontal elements are set across the wavelength dispersed axis while the 578 vertical elements record an image of the input slit. The CCD frame area is centered on the optic axis of the spectrograph and the storage area remains unilluminated. The data of measured absorption spectra of water, deoxygenated and oxygenated hemoglobin are transmitted to the computer 124.

The system provides a dispersion of 1.11 nm per CCD element and a total wavelength scan of 424 nm. Light incident on the CCD camera charges to accumulate in the elements. This charge is then read out and digitized by a 14 bit analogue to digital convertor with an additional programmable gain amplifier. Each count of the ADC can be set equivalent to 10 to 40 electrons. Then, the changes in intensity of absorption spectrum of oxygenated hemoglobin, the changes in intensity of absorption spectrum of deoxygenated hemoglobin and the intensity of absorption spectrum of water are obtained by the computer 124 based on the measured spectrum.

The medium to be interrogated, the reference compound, the substance of interest are not limited to the above-described ones but the medium may be a human or animal limb which comprises of three regions, cortical bone, skeletal muscle and surface adipose tissue, and the reference compounds are tissue water and lipid, and changes in concentration of oxyhemoglobin and deoxyhemoglobin and changes in the redox state of cytochrome oxidase within the skeletal muscle are measured. Alternately, the medium is a human or animal limb, and the reference compounds are tissue water, lipid and deoxyhemoglobin, and changes in concentration of oxyhemoglobin and deoxyhemoglobin and changes in the redox state of cytochrome oxidase within the skeletal muscle are determined.

In cases where it is deemed desirable to have available other reference compounds in addition to those already present in the medium, e.g. if time-resolved estimates of pathlength are unavailable, if water concentrations are not sufficiently distinct amongst certain regions of interest or if it is desired simply to improve the robustness of the partial differential pathlength estimates by providing additional equations, such additional compounds can in principle be introduced from the external environment. Specific examples include the addition of the contrast agent indocyanine-green via injection into the arterial blood supply. In this case it may be assumed that the indocyanine-green concentration will be low in poorly perfused regions such as adipose and cortical bone, whilst its concentration in well perfused regions may be estimated by performing suitable analysis of arterial and venous blood samples.

What is claimed is:

1. A method of determining a change in concentration of at least one subject substance in one region of a plurality of regions of a medium, the one region being adaptable to both absorb and scatter radiation, substantially all of the change in concentration of the at least one subject substance in the medium occurring in the one region of the plurality of regions, said method comprising:

introducing into and propagating through the medium first interrogating radiation which is penetrative of the medium;

detecting the first interrogating radiation which has propagated through the medium and determining a total differential pathlength traversed by the first interrogating radiation in the medium;

identifying a plurality of reference substances, each of which possesses a sufficiently distinct specific absorption coefficient to interrogating radiation and a known concentration in each region of the plurality of regions of the medium, the concentration of each of the plurality of reference substances in the one region being different from the concentration of the same reference substance in each of the other regions of the plurality of regions of the medium;

for each reference substance of the plurality of reference substances, introducing into and propagating through the medium second interrogating radiation which is penetrative of the medium, detecting and spectrometrically analyzing the second interrogating radiation which has propagated through the medium, and determining an intensity of a spectral absorption feature of the reference substance;

determining a partial differential pathlength of the one region by simultaneously solving a first linearly independent equation for each reference substance and a second equation, the first and second equations respectively being expressed as follows:

$$a_i = \sum_{j=1}^{n} C_{ij} \cdot \epsilon_i \cdot Z_j$$

$$Z_T = \sum_{j=1}^{n} Z_j$$

where $a_i$ is the intensity of the spectral absorption feature of the reference substance;

$C_{ij}$ is the known concentration of the reference substance in the region j of the plurality of regions;

$\epsilon_i$ is the absorption coefficient of the reference substance;

$Z_T$ is the total differential pathlength;

$Z_j$ is a partial differential pathlength of the radiation in the region j of the plurality of regions; and n is a total number of regions in the plurality of regions;

introducing into and propagating through the medium third interrogating radiation which is penetrative of the medium;

detecting and spectrometrically analyzing the third interrogating radiation which has propagated through the medium and determining a change in an intensity of a spectral feature of the at least one subject substance; and obtaining the change in concentration of the at least one subject substance in the one region of the plurality of regions of the medium by solving a third equation, the third equation being expressed as follows:

$$C = A/(\epsilon \cdot Z)$$

where

C is the change in concentration of the at least one subject substance in the one region of the plurality of regions of the medium A is the change in the intensity of the spectral feature of the at least one subject substance;

$\epsilon$ is an absorption coefficient of the at least subject substance; and

Z is the partial differential pathlength of the one region.

2. A method according to claim 1, wherein said step of determining the total differential pathlength is performed by a time-of-flight or phase delay technique.

3. A method according to claim 1, wherein the second interrogating radiation is electromagnetic radiation in the near-infrared part of the spectrum, wherein the medium is selected from the group consisting of a human head and an animal head, wherein the plurality of regions comprises a brain region and a skull region, wherein the plurality of reference substances includes tissue water, and wherein said step of obtaining the change in concentration of the at least one subject substance comprises determining changes in concentration of oxyhemoglobin and deoxyhemoglobin and changes in redox state of cytochrome oxidase within the brain.

4. A method according to claim 1, wherein the second interrogating radiation is electromagnetic radiation in the near-infrared part of the spectrum, wherein the medium is selected from the group consisting of a human limb and an animal limb, wherein the plurality of regions comprises cortical bone, skeletal muscle and surface adipose tissue, wherein the plurality of reference substances are tissue water and lipid, and wherein said step of obtaining the change in concentration of the at least one subject substance comprises determining changes in concentration of oxyhemoglobin and deoxyhemoglobin and changes in redox state of cytochrome oxidase within the skeletal muscle.

5. A method according to claim 1, wherein the second interrogating radiation is electromagnetic radiation in the near-infrared part of the spectrum, wherein the medium is selected from the group consisting of a human limb and an animal limb, wherein the plurality of regions comprises cortical bone, skeletal muscle and surface adipose tissue, wherein the plurality of reference substances are tissue water, lipid and deoxyhemoglobin, and wherein said step of obtaining the change in concentration of the at least one subject substance comprises determining changes in concentration of oxyhemoglobin and deoxyhemoglobin and changes in redox state of cytochrome oxidase within the skeletal muscle, said method further comprising determining a concentration of deoxyhemoglobin in the skeletal muscle by blood samples, biopsy samples, or blood and biopsy samples, and setting a concentration of deoxyhemoglobin in the adipose tissue and the cortical bone as zero.

6. A method according to claim 1, wherein one or more of the plurality of reference substances are introduced from the external environment into the medium.

7. A method according to claim 6, further comprising establishing the concentrations of the introduced reference substances by exploiting differential accumulation rates within the regions containing the introduced reference substances.

8. A method according to claim 6, further comprising establishing the concentrations of the introduced reference substances by exploiting differential transit times of the introduced reference substances between a spatial location of introduction of the introduced reference substances and spatial locations of the regions of the medium.

9. A method according to claim 6, wherein the introduced reference substances are indocyanine-green, saline solution, and deuterium-oxide.

10. A method of determining a change in concentration of at least one subject substance in one region of a plurality of regions of a medium, the one region being adaptable to both absorb and scatter radiation, substantially all of the change in concentration of the at least one subject substance in the medium occurring in the one region of the plurality of regions, said method comprising:

introducing into and propagating through the medium first interrogating radiation which is penetrative of the medium;

detecting the first interrogating radiation which has propagated through the medium and determining a total differential pathlength traversed by the first interrogating radiation in the medium;

identifying at least one reference substance, the at least one reference substance possessing a sufficiently distinct specific absorption coefficient to the first interrogating radiation and a known concentration in each region of the plurality of regions of the medium;

introducing into and propagating through the medium second interrogating radiation which is penetrative of the medium, detecting and spectrometrically analyzing the second interrogating radiation which has propagated through the medium, and determining an intensity of a spectral feature of the at least one reference substance;

introducing into and propagating through the medium third interrogating radiation which is penetrative of the medium;

detecting and spectrometrically analyzing the third interrogating radiation which has propagated through the medium and determining a change in an intensity of a spectral feature of the at least one subject substance;

determining a partial differential pathlength of the one region by simultaneously solving first and second equations, the first and second equations respectively being expressed as follows:

$$a_{ref} = \sum_{j=1}^{n} C_j \cdot \epsilon_{ref} \cdot Z_j$$

$$Z_T = \sum_{j=1}^{n} Z_j$$

where $a_{ref}$ is the intensity of the spectral feature of the at least one reference substance;

$C_j$ is the known concentration of the at least one reference substance in region j of the plurality of regions;

$\epsilon_{ref}$ is the absorption coefficient of the at least one reference substance;

$Z_j$ is a partial differential pathlength in the region j; and $Z_T$ is the total differential pathlength;

n is a total number of regions in the plurality of regions; and obtaining the change in concentration of the at least one subject substance in the one region of the plurality of regions of the medium by solving a third equation, the third equation being expressed as follows:

$$C = A/(\epsilon \cdot Z)$$

where

A is the change in the intensity of the spectral feature of the at least one subject substance;

C is the change in concentration of the at least one subject substance in the one region of the plurality of regions of the medium;

$\epsilon$ is an absorption coefficient of the at least subject substance; and

Z is the partial differential pathlength of the one region.

11. A method according to claim 10, wherein said step of determining the total differential pathlength traversed by the first interrogating radiation in the medium comprises measuring a time required for the first interrogating radiation to propagate from a point of entry into the medium to a point of exit from the medium, and multiplying the measured time by the speed of light.

12. A method according to claim 10, wherein said step of determining the total differential pathlength traversed by the first interrogating radiation in the medium comprises measuring a phase delay induced in the first interrogating radiation which propagates through the medium, and determining a phase shift and multiplying the phase shift by a wavelength of a sinusoidal intensity modulation within the medium.

13. A method according to claim 10, wherein the second interrogating radiation is electromagnetic radiation in the near-infrared part of the spectrum, wherein the medium is selected from the group consisting of a human head and an animal head, wherein the plurality of regions comprises a brain region and a skull region, wherein the at least one reference substance is tissue water, and wherein said step of obtaining the change in concentration of the at least one subject substance comprises determining changes in concentration of oxyhemoglobin and deoxyhemoglobin and changes in redox state of cytochrome oxidase within the brain.

14. A method according to claim 10, wherein the second interrogating radiation is electromagnetic radiation in the near-infrared part of the spectrum, wherein the medium is selected from the group consisting of a human limb and an animal limb, wherein the plurality of regions comprises cortical bone, skeletal muscle and surface adipose tissue, wherein the at least one reference substance comprises tissue water and lipid, and wherein said step of obtaining the change in concentration of the at least one subject substance comprises determining changes in concentration of oxyhemoglobin and deoxyhemoglobin and changes in redox state of cytochrome oxidase within the skeletal muscle.

15. A method according to claim 10, wherein the second interrogating radiation is electromagnetic radiation in the near-infrared part of the spectrum, wherein the medium is selected from the group consisting of a human limb and an animal limb, wherein the plurality of regions comprises cortical bone, skeletal muscle and surface adipose tissue, wherein the at least one reference substance comprises tissue water, lipid and deoxyhemoglobin, and wherein said step of obtaining the change in concentration of the at least one subject substance comprises determining changes in concentration of oxyhemoglobin and deoxyhemoglobin and changes in redox state of cytochrome oxidase within the skeletal muscle, said method further comprising determining a concentration of deoxyhemoglobin in the skeletal muscle by blood samples, biopsy samples, or blood and biopsy samples, and setting a concentration of deoxyhemoglobin in the adipose tissue and the cortical bone as zero.

16. A method according to claim 10, wherein the at least one reference substance includes a plurality of reference substances, and one or more of which are introduced from the external environment into the medium.

17. A method according to claim 16, further comprising establishing the concentrations of the introduced reference substances by exploiting differential accumulation rates within the regions containing the introduced reference substances.

18. A method according to claim 16, further comprising establishing the concentrations of the introduced reference substances by exploiting differential transit times of the introduced reference substances between a spatial location of introduction of the introduced reference substances and spatial locations of the regions of the medium.

19. A method according to claim 16, wherein the introduced reference substances are indocyanine-green, saline solution, and deuterium-oxide.

20. An apparatus for determining a change in concentration of at least one subject substance in one region of a plurality of regions of a medium, the one region being adaptable to both absorb and scatter radiation, substantially all of the change in concentration of the at least one subject substance in the medium occurring in the one region of the plurality of regions, the plurality of regions each comprising at least one reference substance possessing a distinct specific absorption coefficient to a specific radiation and a known concentration, said apparatus comprising:

a first light source for introducing into and propagating through the medium first interrogating radiation which is penetrative of the medium;

a first photodetecting unit for detecting the first interrogating radiation which has propagated through the medium to measure an intensity of a spectral feature of the at least one subject substance or the at least one reference substance;

a second light source for introducing into and propagating through the medium second interrogating radiation which is penetrative of the medium;

a second photodetecting unit for detecting the second interrogating radiation which has propagated through the medium to measure a total differential pathlength traversed by the second interrogating radiation in the medium;

a first processing unit for receiving the intensity of the spectral feature of the at least one subject substance or at least one reference substance from said first photodetecting unit, for receiving the total differential pathlength from said second photodetecting unit, and for determining the partial differential pathlength of the one region by solving first and second equations, the first and second equations being expressed as follows:

$$a_{ref} = \sum_{j=1}^{n} C_j \cdot \epsilon_{ref} \cdot Z_j$$

$$Z_T = \sum_{j=1}^{n} Z_j$$

where $a_{ref}$ is said intensity of said spectral feature of the at least one reference substance;

$C_j$ is the known concentration of the at least one reference substance in region j of the plurality of regions;

$\epsilon_{ref}$ is the absorption coefficient of said at least one reference substance;

$Z_j$ is a partial differential pathlength in the region j; and $Z_T$ is the total differential pathlength;

n is a total number of regions in the plurality of regions; and a second processing unit for determining the change in concentration of the at least one substance in the one region of the plurality of regions of the medium by a third equation, the third equation being expressed as follows:

$$C = A/(\epsilon \cdot Z)$$

where

A is the change in the intensity of the spectral feature of the at least one subject substance;

C is the change in concentration of the at least one subject substance in the one region of the plurality of regions of the medium;

$\epsilon$ is an absorption coefficient of the at least subject substance; and

Z is the partial differential pathlength of the one region.

21. An apparatus according to claim 20, further comprising a display unit for receiving the change in concentration of the at least one subject substance from said second processing unit and for displaying the change in concentration of the at least one subject substance, said display unit being digital or analog.

22. An apparatus according to claim 21, wherein said display unit is a CRT.

23. An apparatus according to claim 20, wherein said second photodetecting unit is constructed and arranged to measure a time required for the first interrogating radiation to propagate from a point of entry into the medium to a point of exit from the medium and to obtain the total differential pathlength traversed by the interrogating radiation in the medium by multiplying the measured time by the speed of light.

24. An apparatus according to claim 23, wherein said second photodetecting unit is a streak camera.

25. An apparatus according to claim 23, wherein said second light source is a laser light source.

26. An apparatus according to claim 20, wherein said second photodetecting unit is constructed and arranged to measure a phase delay induced in the second interrogating radiation which propagates through the medium and to obtain the total differential pathlength traversed by the second interrogating radiation in the medium by multiplying a measured phased shift by a wavelength of a sinusoidal intensity modulation within the medium.

27. An apparatus according to claim 26, wherein both said second light source and said second photodetecting unit comprise an intensity modulated optical spectrometer.

28. An apparatus according to claim 20, wherein both said first light source and said first photodetecting unit comprise a CCD spectroscopy system.

29. An apparatus according to claim 20, wherein said first light source is a DC lamp.

30. An apparatus according to claim 20, wherein said first photodetecting unit is a spectroscope.

31. An apparatus according to claim 20, wherein said first light source produces electromagnetic radiation in the near-frared part of the spectrum, wherein the medium is selected from the group consisting of a human head an an animal head, wherein the plurality of regions comprises a brain region and a skull region, wherein the at least one reference substance is tissue water, and wherein said second processing unit is adapted to determine changes in concentration of oxyhemoglobin and deoxyhemoglobin and changes in redox state of cytochrome oxidase within the brain.

32. An apparatus according to claim 20, wherein the first light source produces electromagnetic radiation in the near-infrared part of the spectrum, wherein the medium is selected from the group consisting of a human limb and an animal limb, wherein the plurality of regions comprises cortical bone, skeletal muscle and surface adipose tissue, wherein the at least one reference substance comprises tissue water and lipid, and wherein said second processing unit is adapted to determine changes in concentration of oxyhemoglobin and deoxyhemoglobin and changes in redox state of cytochrome oxidase within the skeletal muscle.

33. An apparatus according to claim 20, wherein the first light source produces electromagnetic radiation in the near-infrared part of the spectrum, wherein the medium is selected from the group consisting of a human limb and an animal limb, wherein the plurality of regions comprises cortical bone, skeletal muscle and surface adipose tissue, wherein the at least one reference substance comprises tissue water, lipid and deoxyhemoglobin, wherein said second processing unit is adapted to determine changes in concentration of oxyhemoglobin and deoxyhemoglobin and changes in redox state of cytochrome oxidase within the skeletal muscle, and wherein said apparatus is adapted to determine a concentration of deoxyhemoglobin in the skeletal muscle by blood samples, biopsy samples, or blood and biopsy samples, and set a concentration of deoxyhemoglobin in the adipose tissue and the cortical bone as zero.

* * * * *